(12) United States Patent
Vitali et al.

(10) Patent No.: US 12,116,469 B2
(45) Date of Patent: Oct. 15, 2024

(54) STERICALLY HINDERED AMINE STABILIZER MIXTURES

(71) Applicant: BASF SE, Ludwigshafen am Rhein (DE)

(72) Inventors: Manuele Vitali, Pontecchio Marconi BO (IT); Elisa Montroni, Pontecchio Marconi BO (IT); Matteo Pori, Pontecchio Marconi BO (IT); Elena Capito, Pontecchio Marconi BO (IT); Christian Kranemann, Schweizerhalle (CH)

(73) Assignee: BASF SE, Ludwigshafen am Rhein (DE)

( * ) Notice: Subject to any disclaimer, the term of this patent is extended or adjusted under 35 U.S.C. 154(b) by 425 days.

(21) Appl. No.: 17/437,176

(22) PCT Filed: Mar. 4, 2020

(86) PCT No.: PCT/EP2020/055754
§ 371 (c)(1),
(2) Date: Sep. 8, 2021

(87) PCT Pub. No.: WO2020/182587
PCT Pub. Date: Sep. 17, 2020

(65) Prior Publication Data
US 2023/0159727 A1    May 25, 2023

(30) Foreign Application Priority Data

Mar. 8, 2019  (EP) ..................... 19161580

(51) Int. Cl.
*C08K 5/3492* (2006.01)
*C07D 401/14* (2006.01)

(52) U.S. Cl.
CPC ........ *C08K 5/34926* (2013.01); *C07D 401/14* (2013.01); *C08K 2201/014* (2013.01)

(58) Field of Classification Search
CPC .......... C08K 5/34926; C08K 2201/014; C08K 5/005; C07D 401/14; C08L 23/06
See application file for complete search history.

(56) References Cited

U.S. PATENT DOCUMENTS 4,177,186 A    12/1979 Rody et al.
4,412,021 A    10/1983 Karrer
(Continued)

FOREIGN PATENT DOCUMENTS

CN    105693698 A    6/2016
EP      0101411 A2    2/1984
(Continued)

OTHER PUBLICATIONS

Vitali et al, WO2015173190-MT (Year: 2015).*
(Continued)

*Primary Examiner* — Liam J Heincer
*Assistant Examiner* — Zhen Liu
(74) *Attorney, Agent, or Firm* — ArentFox Schiff LLP

(57) ABSTRACT

The present invention relates to mixtures of sterically hindered amines of the formulae (1) and (2)

(Continued)

-continued

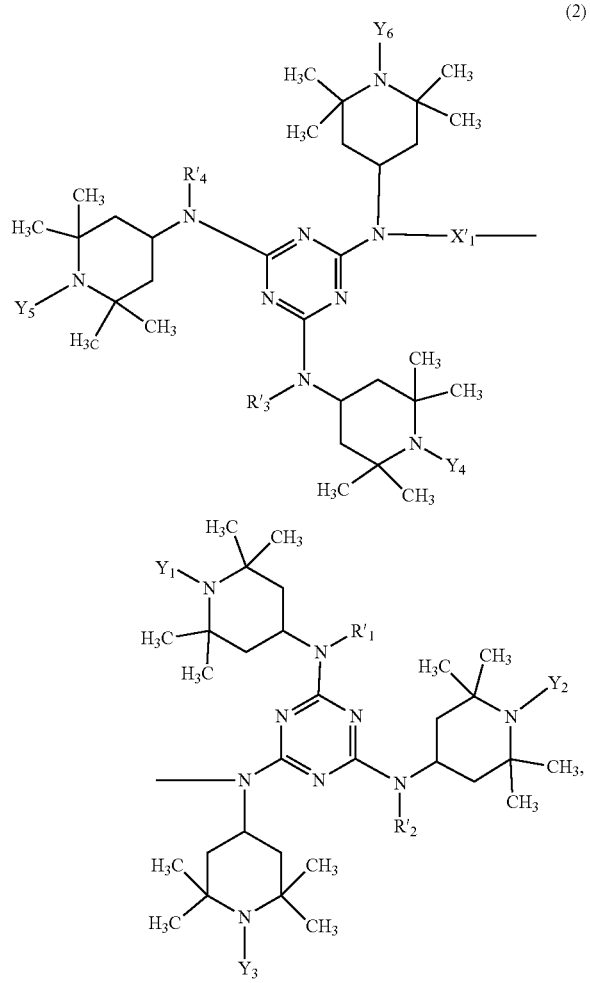

(2)

wherein
at least one of the radicals $Z_1$, $Z_2$, $Z_3$, $Z_4$, $Z_5$ and $Z_6$ is $C_1$-$C_{18}$ alkyloxy or $C_5$-$C_7$ cycloalkyloxy and the remaining of the radicals $Z_1$, $Z_2$, $Z_3$, $Z_4$, $Z_5$ and $Z_6$ are hydrogen, hydroxy, $C_1$-$C_{18}$ alkyloxy or $C_5$-$C_7$ cycloalkyloxy, and at least one of the radicals $Y_1$, $Y_2$, $Y_3$, $Y_4$, $Y_5$ and $Y_6$ is a group of formula —$CH_2$—CH=CH—R and the remaining of the radicals $Y_1$, $Y_2$, $Y_3$, $Y_4$, $Y_5$ and $Y_6$ are hydrogen or a group of formula —$CH_2$—CH=CH—R, and the other substituents are as defined according to the present invention, methods for stabilization of an organic material, and a process for the preparation of compounds of formula (1').

14 Claims, No Drawings

(56) References Cited

U.S. PATENT DOCUMENTS

| | | | |
|---|---|---|---|
| 9,932,343 B2* | 4/2018 | Alexander | C07D 513/04 |
| 10,323,215 B2* | 6/2019 | Fuchs | C08L 33/02 |

FOREIGN PATENT DOCUMENTS

| | | | |
|---|---|---|---|
| GB | 1511773 A | | 5/1978 |
| TW | 201819506 A | | 6/2018 |
| WO | 2004035671 A1 | | 4/2004 |
| WO | 2006/048389 A1 | | 5/2006 |
| WO | 2011/029744 A1 | | 3/2011 |
| WO | WO2015173190 | * | 11/2015 ............. B32B 27/32 |

OTHER PUBLICATIONS

European Search Report for EP Patent Application No. 19161580.6, Issued on Jul. 19, 2019, 4 pages.
International Search Report for PCT Patent Application No. PCT/EP2020/055754, Issued on Jul. 1, 2020, 4 pages.

* cited by examiner

STERICALLY HINDERED AMINE STABILIZER MIXTURES

CROSS-REFERENCE TO RELATED APPLICATIONS

This application is a National Stage Entry of PCT/EP2020/055754, filed Mar. 4, 2020, which claims priority to EP application No. 19161580.6 filed Mar. 8, 2019, the disclosures of each of which are hereby incorporated by reference in their entirety.

The present invention relates to mixtures of sterically hindered amines of the formulae (1) and (2) as defined hereinafter, methods for stabilization of an organic material, and a process for the preparation of specific compounds of formula (1).

Sterically hindered amines are known to be efficient stabilizers for organic materials against the harmful effect of light and heat—especially for synthetic polymers like polyolefins. For example, agricultural films produced from polyolefins are stabilized by sterically hindered amine stabilizers, since light transmission has got a major impact on the growth of crops and a sustainable light transmission depends on the long-term stability of the film.

There is still a need for further sterically hindered amine stabilizers and mixtures of these, which provide a further improvement of the long-term stabilization of organic materials.

The present invention relates in particular to an additive mixture comprising a compound of formula (1)

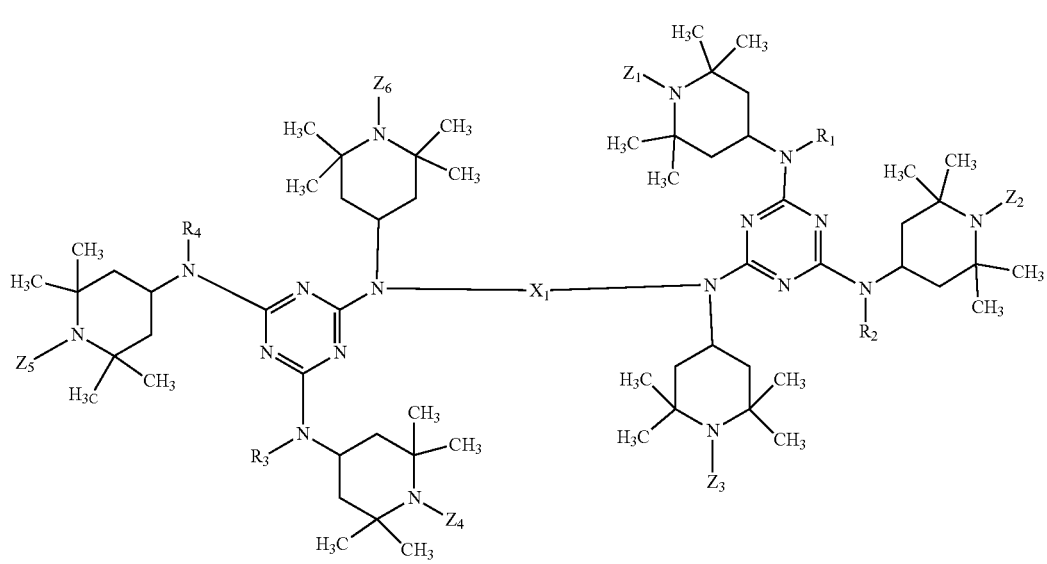

(1)

and a compound of formula (2)

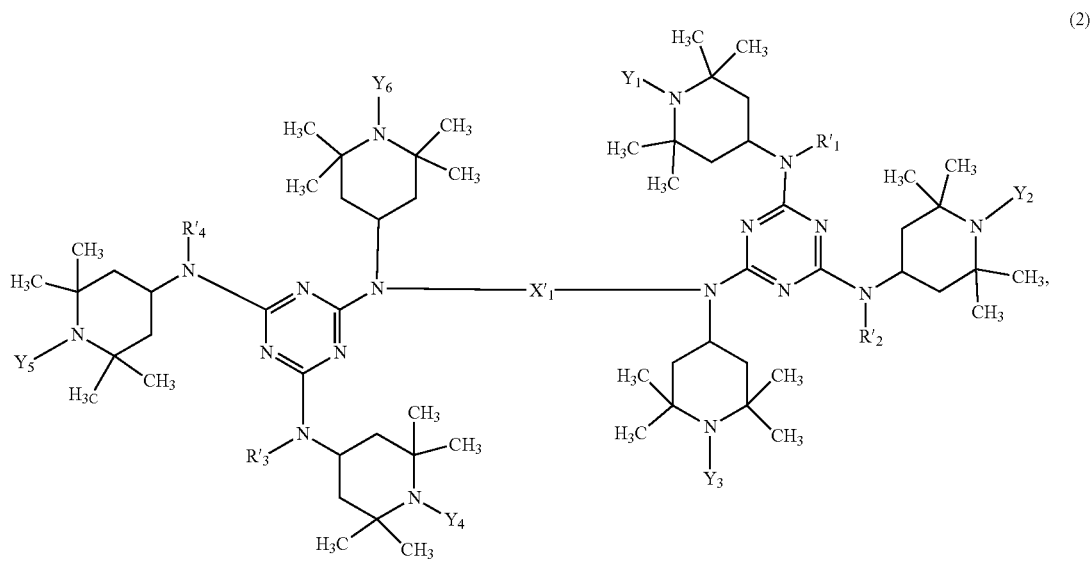

(2)

wherein $R_1$, $R_2$, $R_3$, $R_4$, $R'_1$, $R'_2$, $R'_3$ and $R'_4$ are independently from each other hydrogen or $C_1$-$C_{18}$ alkyl, $X_1$ and $X'_1$ are independently from each other $C_2$-$C_{12}$ alkylene or $C_3$-$C_{12}$ alkylene substituted by hydroxyl;

at least one of the radicals $Z_1$, $Z_2$, $Z_3$, $Z_4$, $Z_5$ and $Z_6$ is $C_1$-$C_{18}$ alkyloxy or $C_5$-$C_7$ cycloalkyloxy and the remaining of the radicals $Z_1$, $Z_2$, $Z_3$, $Z_4$, $Z_5$ and $Z_6$ are independently from each other hydrogen, hydroxy, $C_1$-$C_{18}$ alkyloxy or $C_5$-$C_7$ cycloalkyloxy, at least one of the radicals $Y_1$, $Y_2$, $Y_3$, $Y_4$, $Y_5$ and $Y_6$ is a group of formula —$CH_2$—$CH$=$CH$—$R$ and the remaining of the radicals $Y_1$, $Y_2$, $Y_3$, $Y_4$, $Y_5$ and $Y_6$ are independently from each other hydrogen or a group of formula —$CH_2$—$CH$=$CH$—$R$, and R is hydrogen, $C_1$-$C_{18}$ alkyl or $C_5$-$C_7$ cycloalkyl.

$C_1$-$C_{18}$ alkyl and preferably $C_1$-$C_{18}$ alkyl comprises linear and branched alkyl. Examples are methyl, ethyl, n-propyl, 1-methylethyl, n-butyl, 2-methylpropyl, 1-methylpropyl, tert-butyl, pentyl, 1-methylbutyl, 2-methylbutyl, 3-methylbutyl, 1,1-dimethylpropyl, 1-ethylpropyl, tert-butylmethyl, hexyl, 1-methylpentyl, heptyl, isoheptyl, 2-ethylpentyl, 1-propylbutyl, octyl, isooctyl, 1-ethylhexyl, 2-ethylhexyl, 1,1,3,3-tetramethylbutyl, 2,4,4-trimethylpentyl, nonyl, isononyl, neononyl, undecyl, lauryl, tridecyl, tetradecyl, pentadecyl.

More preferred is $C_1$-$C_{12}$ alkyl, especially $C_1$-$C_8$ alkyl, in particular $C_1$-$C_4$ alkyl. A preferred example is butyl, especially n-butyl.

$C_1$-$C_{18}$ alkyloxy comprises unsubstituted and substituted, i.e. by $C_1$-$C_9$ alkyl, alkyloxy. Examples are methyloxy, ethyloxy, propyloxy (=propoxy), butyloxy, hexyloxy, octyloxy and undecyloxy.

Preferred is $C_1$-$C_{12}$ alkyloxy. Preferred examples are methyloxy, ethyloxy, propyloxy, octyloxy and undecyloxy. Highly preferred is $C_1$-$C_4$ alkyloxy, especially propyloxy.

Preference is given to $C_1$-$C_{18}$ alkyloxy, wherein in case of $C_3$-$C_{18}$ alkyloxy both carbon atoms in α- and β-position next to the oxygen are not branched. Examples are methyloxy, ethyloxy, n-propyloxy, n-butyloxy, n-pentyloxy, 3-methylbutyloxy, n-hexyloxy, 3-methylpentyloxy, 4-methylpentyloxy, n-heptyloxy, 3-methylhexyloxy, 4-methylhexyloxy, 5-methylhexyloxy, 3-ethylpentyloxy, 3,4-dimethylpentyloxy, n-octyloxy, 3-methylheptyloxy, 4-methylheptyloxy, 5-methylheptyloxy, 6-methylheptyloxy, 3-ethylhexyloxy, 4-ethylhexyloxy, 3,4-dimethylhexyloxy, 3,5-dimethylhexyloxy, n-nonyloxy, 3-methyloctyloxy, 4-methyloctyloxy, 5-methyloctyloxy, 6-methyloctyloxy, 7-methyloctyloxy, 3-ethylheptyloxy, 4-ethylheptyloxy, 5-ethylheptyloxy, 3,4-dimethylheptyloxy, 3,5-dimethylheptyloxy, 3,6-dimethylheptyloxy, 4,5-dimethylheptyloxy, 4,6-dimethylheptyloxy, 5,6-dimethylheptyloxy, n-undecyloxy, n-lauryloxy, n-tridecyloxy, n-tetradecyloxy, n-pentadecyloxy, n-hexadecyloxy and n-octadecyloxy.

Particular preference is given to $C_3$-$C_{18}$ alkyloxy, more preferably $C_3$-$C_{12}$ alkyloxy, especially $C_3$-$C_8$ alkyloxy, wherein both carbon atoms in α- and β-position next to the oxygen are not branched.

Highly preferred is linear $C_1$-$C_{12}$ alkyloxy, especially linear $C_1$-$C_4$ alkyloxy. Examples are methyloxy, ethyloxy, n-propyloxy, n-butyloxy, n-pentyloxy, n-hexyloxy, n-heptyloxy, n-octyloxy, n-nonyloxy, n-undecyloxy and n-lauryloxy, especially n-propyloxy.

$C_5$-$C_7$ cycloalkyloxy is for example cyclopentyloxy, cyclohexyloxy or cycloheptyloxy, preferably cyclohexyloxy.

$C_5$-$C_7$ cycloalkyl is for example cyclopentyl, cyclohexyl or cycloheptyl, preferably cyclohexyl.

$C_2$-$C_{12}$ alkylene comprises unsubstituted and substituted, i.e. by one or more $C_1$-$C_4$ alkyl, alkylene. Examples are ethylene, propylene, 1-methylethylene, butylene, pentylene, 2-methyl-butylene, hexamethylene and octamethylene.

Preferred is $C_2$-$C_8$ alkylene, in particular $C_2$-$C_6$ alkylene. Preferred examples are hexamethylene, propylene and ethylene, especially hexamethylene.

$C_3$-$C_{12}$ alkylene substituted by hydroxyl comprises no further substituted and further substituted, i.e. by one or more $C_1$-$C_4$ alkyl, alkylene substituted by hydroxyl. Examples are 2-hydroxypropylene, 2-hydroxy-butylene, 2,3-dihydroxybutylene, 2,5-hexamethylene and 2-hydroxy-2-methylpropylene. A preferred example is 2-hydroxypropylene.

$R_1$, $R_2$, $R_3$, $R_4$, $R'_1$, $R'_2$, $R'_3$ and $R'_4$ are preferably $C_1$-$C_{12}$ alkyl, especially $C_1$-$C_8$ alkyl, in particular $C_1$-$C_4$ alkyl. Highly preferred is butyl, especially n-butyl.

R is preferably $C_1$-$C_4$ alkyl, cyclohexyl or hydrogen, preferably $C_1$-$C_4$ alkyl or hydrogen, especially hydrogen.

$X_1$ and $X'_1$ are preferably $C_2$-$C_8$ alkylene, more preferably $C_2$-$C_6$ alkylene, especially hexamethylene.

According to one embodiment all radicals $Z_1$, $Z_2$, $Z_3$, $Z_4$, $Z_5$ and $Z_6$ represent $C_1$-$C_{18}$ alkyloxy or $C_5$-$C_7$ cycloalkyloxy, especially $C_1$-$C_{18}$ alkyloxy.

It is preferred that only one to five radicals of the radicals $Z_1$, $Z_2$, $Z_3$, $Z_4$, $Z_5$ and $Z_6$ are $C_1$-$C_{18}$ alkyloxy or $C_5$-$C_7$ cycloalkyloxy and the remaining of the radicals $Z_1$, $Z_2$, $Z_3$, $Z_4$, $Z_5$ and $Z_6$ are hydrogen or hydroxy. For example, five of these radicals are $C_1$-$C_{18}$ alkyloxy or $C_5$-$C_7$ cycloalkyloxy and the remaining one radical is hydrogen or hydroxy.

More preferably two to five, especially three to five, of the radicals $Z_1$, $Z_2$, $Z_3$, $Z_4$, $Z_5$ and $Z_6$ are $C_1$-$C_{18}$ alkyloxy or $C_5$-$C_7$ cycloalkyloxy and the remaining of the radicals $Z_1$, $Z_2$, $Z_3$, $Z_4$, $Z_5$ and $Z_6$ are hydrogen or hydroxy.

Most preferably four to five, especially five, of the radicals $Z_1$, $Z_2$, $Z_3$, $Z_4$, $Z_5$ and $Z_6$ are $C_1$-$C_{18}$ alkyloxy or $C_5$-$C_7$ cycloalkyloxy and the remaining of the radicals $Z_1$, $Z_2$, $Z_3$, $Z_4$, $Z_5$ and $Z_6$ are hydrogen or hydroxy.

Alternatively, the degree of substitution by $C_1$-$C_{18}$ alkyloxy and $C_5$-$C_7$ cycloalkyloxy can also be expressed in percent (number of the sum of $C_1$-$C_{18}$ alkyloxy and $C_5$-$C_7$ cycloalkyloxy groups in relation to the full substitution by $C_1$-$C_{18}$ alkyloxy and $C_5$-$C_7$ cycloalkyloxy, which are six groups). This is, for example, useful to specify mean values for the degree of substitution in case of mixtures of compounds of formula (1). For such degree of substitution by $C_1$-$C_{18}$ alkyloxy and $C_5$-$C_7$ cycloalkyloxy 50 to 95%, especially 50 to 90% is preferred. More preferred is a degree of substitution of 50 to 85%, especially 60 to 85%.

$Z_1$, $Z_2$, $Z_3$, $Z_4$, $Z_5$ and $Z_6$ in the meaning as $C_1$-$C_{18}$ alkyloxy are preferably $C_1$-$C_8$ alkyloxy, more preferably $C_1$-$C_4$ alkyloxy and especially propyloxy, like n-propyloxy.

$Z_1$, $Z_2$, $Z_3$, $Z_4$, $Z_5$ and $Z_6$ in the meaning as $C_1$-$C_{18}$ alkyloxy are more preferably a group of formula —O—$CH_2$—$CH_2$—$CH_2$—$R$, wherein R is hydrogen or $C_1$-$C_{15}$ alkyl, preferably hydrogen.

$Z_1$, $Z_2$, $Z_3$, $Z_4$, $Z_5$ and $Z_6$ in the meaning as $C_1$-$C_{18}$ alkyloxy or $C_5$-$C_7$ cycloalkyloxy are preferably $C_1$-$C_{18}$ alkyloxy.

According to a further embodiment all radicals $Y_1$, $Y_2$, $Y_3$, $Y_4$, $Y_5$ and $Y_6$ represent a group of formula —$CH_2$—$CH$=$CH$—$R$.

It is preferred that only one to five radicals of the radicals $Y_1$, $Y_2$, $Y_3$, $Y_4$, $Y_5$ and $Y_6$ are a group of formula —$CH_2$—$CH$=$CH$—$R$ and the remaining of the radicals $Y_1$, $Y_2$, $Y_3$, $Y_4$, $Y_5$ and $Y_6$ are hydrogen. For example, five of these radicals are a group of formula —$CH_2$—CH=CH—R and the remaining one is hydrogen.

More preferably two to five, especially three to five, of the radicals $Y_1$, $Y_2$, $Y_3$, $Y_4$, $Y_5$ and $Y_6$ are a group of formula —$CH_2$—CH=CH—R and the remaining of the radicals $Y_1$, $Y_2$, $Y_3$, $Y_4$, $Y_5$ and $Y_6$ are hydrogen.

Most preferably four to five, especially five, of the radicals $Y_1$, $Y_2$, $Y_3$, $Y_4$, $Y_5$ and $Y_6$ are a group of formula —$CH_2$—CH=CH—R and the remaining of the radicals $Y_1$, $Y_2$, $Y_3$, $Y_4$, $Y_5$ and $Y_6$ are hydrogen.

Alternatively, the degree of substitution by a group of formula —$CH_2$—CH=CH—R can also be expressed in percent (number of —$CH_2$—CH=CH—R groups in relation to the full substitution by six —$CH_2$—CH=CH—R groups). This is, for example, useful to specify mean values for the degree of substitution in case of mixtures of compounds of formula (2). For such degree of substitution by a group of formula —$CH_2$—CH=CH—R 40 to 95%, especially 40 to 90% is preferred. More preferred is a degree of substitution of 50 to 90%, especially 60 to 90%.

More preferably, one to five radicals of the radicals $Z_1$, $Z_2$, $Z_3$, $Z_4$, $Z_5$ and $Z_6$ are $C_1$-$C_{18}$ alkyloxy or $C_5$-$C_7$ cycloalkyloxy and the remaining of the radicals $Z_1$, $Z_2$, $Z_3$, $Z_4$, $Z_5$ and $Z_6$ are hydrogen or hydroxy, and one to five radicals of the radicals $Y_1$, $Y_2$, $Y_3$, $Y_4$, $Y_5$ and $Y_6$ are a group of formula —$CH_2$—CH=CH—R and the remaining of the radicals $Y_1$, $Y_2$, $Y_3$, $Y_4$, $Y_5$ and $Y_6$ are hydrogen.

In the formula —$CH_2$—CH=CH—R, the radical R is preferably hydrogen, $C_1$-$C_{18}$ alkyl or cyclohexyl, more preferably hydrogen or $C_1$-$C_{18}$ alkyl, especially hydrogen.

Of special interest are additive mixtures, wherein
$R_1$, $R_2$, $R_3$, $R_4$, $R'_1$, $R'_2$, $R'_3$ and $R'_4$ are $C_1$-$C_{12}$ alkyl,
$X_1$ and $X'_1$ are $C_2$-$C_8$ alkylene,
one to five radicals of the radicals $Z_1$, $Z_2$, $Z_3$, $Z_4$, $Z_5$ and $Z_6$ are $C_1$-$C_{18}$ alkyloxy or $C_5$-$C_7$ cycloalkyloxy and the remaining of the radicals $Z_1$, $Z_2$, $Z_3$, $Z_4$, $Z_5$ and $Z_6$ are hydrogen or hydroxy, especially hydrogen,
one to five radicals of the radicals $Y_1$, $Y_2$, $Y_3$, $Y_4$, $Y_5$ and $Y_6$ are a group of formula —$CH_2$—CH=CH—R and the remaining of the radicals $Y_1$, $Y_2$, $Y_3$, $Y_4$, $Y_5$ and $Y_6$ are hydrogen, and
R is hydrogen or cyclohexyl. $Z_1$, $Z_2$, $Z_3$, $Z_4$, $Z_5$ and $Z_6$ as $C_1$-$C_{18}$ alkyloxy are preferably n-propyloxy.

Of high importance are additive mixtures, wherein
$R_1$, $R_2$, $R_3$, $R_4$, $R'_1$, $R'_2$, $R'_3$ and $R'_4$ are $C_1$-$C_{12}$ alkyl,
$X_1$ and $X'_1$ are $C_2$-$C_8$ alkylene,
one to five radicals of the radicals $Z_1$, $Z_2$, $Z_3$, $Z_4$, $Z_5$ and $Z_6$ are $C_1$-$C_{18}$ alkyloxy and the remaining of the radicals $Z_1$, $Z_2$, $Z_3$, $Z_4$, $Z_5$ and $Z_6$ are hydrogen or hydroxy, especially hydrogen,
one to five radicals of the radicals $Y_1$, $Y_2$, $Y_3$, $Y_4$, $Y_5$ and $Y_6$ are a group of formula —$CH_2$—CH=CH—R and the remaining of the radicals $Y_1$, $Y_2$, $Y_3$, $Y_4$, $Y_5$ and $Y_6$ are hydrogen, and
R is hydrogen. $Z_1$, $Z_2$, $Z_3$, $Z_4$, $Z_5$ and $Z_6$ as $C_1$-$C_{18}$ alkyloxy are preferably n-propyloxy.

Most preferred as compounds of formula (1) are compounds of the following formula (1-A)

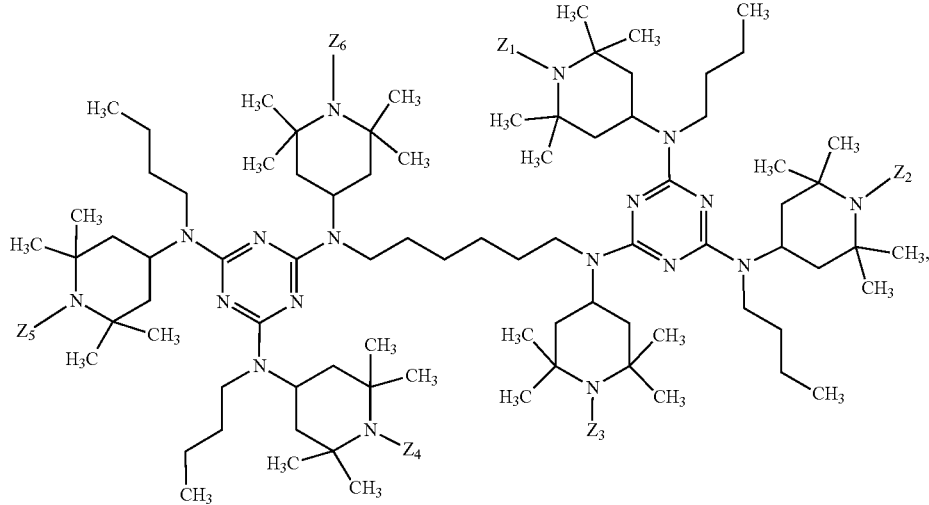

(1-A)

wherein for $Z_1$, $Z_2$, $Z_3$, $Z_4$, $Z_5$ and $Z_6$ the definitions and preferences given hereinbefore apply.

Most preferred as compounds of formula (2) are compounds of the following formula (2-A)

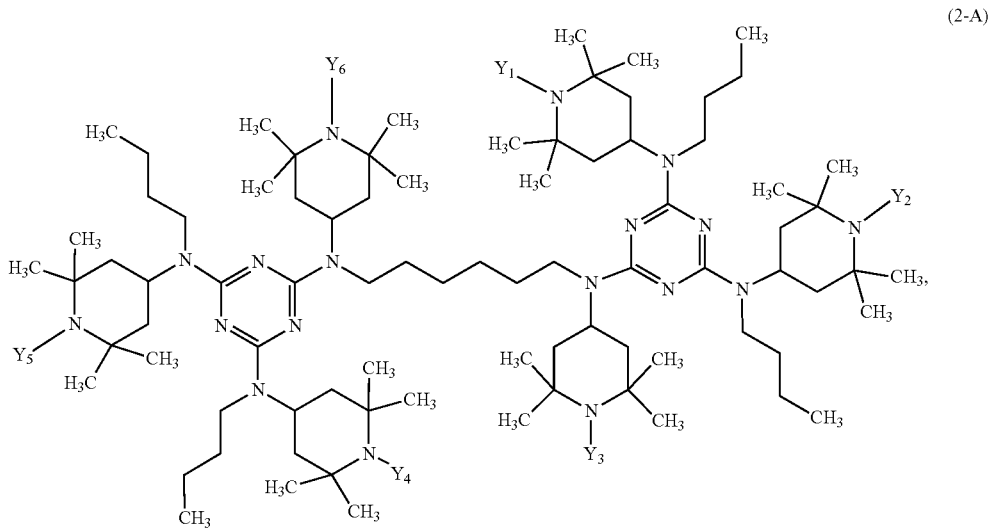

(2-A)

wherein for $Y_1$, $Y_2$, $Y_3$, $Y_4$, $Y_5$ and $Y_6$ the definitions and preferences given hereinbefore apply.

Highly preferred is a mixture of the compounds of formulae (1-A) and (2-A).

The weight ratio of compound of formula (1) to compound of formula (2) is preferably 1:99 to 99:1, especially 5:95 to 95:5. A weight ratio of 10:90 to 90:10, especially 20:80 to 80:20, is highly preferred. Of special interest is a weight ratio of 30:70 to 70:30, especially 40:60 to The compounds of formula (1) or formula (2) can be prepared according to known methods, for example as given in WO 2011/029744.

A further embodiment of this invention is a composition comprising
a) an organic material which is susceptible to oxidative, thermal or light-induced degradation; and
b) a mixture of the compounds of formulae (1) and (2).

For example, an organic material comprises natural, semi-natural and synthetic polymers, especially synthetic polymers.

Examples for polymers are:
1. Polymers of monoolefins and diolefins, for example polypropylene, polyisobutylene, poly-but-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).
b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1., for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1. above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$-$C_9$) including hydrogenated modifications thereof (e.g. tackifiers) and mixtures of polyalkylenes and starch.

Homopolymers and copolymers from 1.-4. may have any stereostructure including syndiotactic, isotactic, hemi-isotactic or atactic; where atactic polymers are preferred. Stereoblock polymers are also included.

5. Polystyrene, poly(p-methylstyrene), poly(α-methylstyrene).

6. Aromatic homopolymers and copolymers derived from vinyl aromatic monomers including styrene, α-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

6b. Hydrogenated aromatic polymers derived from hydrogenation of polymers mentioned under 6.), especially including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under 6a.

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from 04-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9. with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1. above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or polym-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).
17. Polyureas, polyimides, polyamide-imides, polyetherimides, polyesterimides, polyhydantoins and polybenzimidazoles.
18. Polyesters derived from dicarboxylic acids and diols and/or from hydroxycarboxylic acids or the corresponding lactones or lactides, for example polyethylene terephthalate, polybutylene terephthalate, poly-1,4-dimethylolcyclohexane terephthalate, polyalkylene naphthalate and polyhydroxybenzoates as well as copolyether esters derived from hydroxyl-terminated polyethers, and also polyesters modified with polycarbonates or MBS. Copolyesters may comprise, for example—but are not limited to—polybutylenesuccinate/terephtalate, polybutyleneadipate/terephthalate, polytetramethyleneadipate/terephthalate, polybutylensuccinate/adipate, polybutylensuccinate/carbonate, poly-3-hydroxybutyrate/octanoate copolymer, poly-3-hydroxybutyrate/hexanoate/decanoate terpolymer. Furthermore, aliphatic polyesters may comprise, for example—but are not limited to—the class of poly (hydroxyalkanoates), in particular, poly(propiolactone), poly(butyrolactone), poly(pivalolactone), poly (valerolactone) and poly(caprolactone), polyethylenesuccinate, polypropylenesuccinate, polybutylenesuccinate, polyhexamethylenesuccinate, polyethyleneadipate, polypropyleneadipate, polybutyleneadipate, polyhexamethyleneadipate, polyethyleneoxalate, polypropyleneoxalate, polybutyleneoxalate, polyhexamethyleneoxalate, polyethylenesebacate, polypropylenesebacate, polybutylenesebacate and polylactic acid (PLA) as well as corresponding polyesters modified with polycarbonates or MBS. The term 'polylactic acid (PLA)' designates a homo-polymer of preferably poly-L-lactide and any of its blends or alloys with other polymers; a co-polymer of lactic acid or lactide with other monomers, such as hydroxy-carboxylic acids, like for example glycolic acid, 3-hydroxy-butyric acid, 4-hydroxy-butyric acid, 4-hydroxy-valeric acid, 5-hydroxy-valeric acid, 6-hydroxy-caproic acid and cyclic forms thereof; the terms 'lactic acid' or 'lactide' include L-lactic acid, D-lactic acid, mixtures and dimers thereof, i.e. L-lactide, D-lactide, meso-lactide and any mixtures thereof.
19. Polycarbonates and polyester carbonates.
20. Polyketones.
21. Polysulfones, polyether sulfones and polyether ketones.
22. Crosslinked polymers derived from aldehydes on the one hand and phenols, ureas and melamines on the other hand, such as phenol/formaldehyde resins, urea/formaldehyde resins and melamine/formaldehyde resins.
23. Drying and non-drying alkyd resins.
24. Unsaturated polyester resins derived from copolyesters of saturated and unsaturated dicarboxylic acids with polyhydric alcohols and vinyl compounds as crosslinking agents, and also halogen-containing modifications thereof of low flammability.
25. Crosslinkable acrylic resins derived from substituted acrylates, for example epoxy acrylates, urethane acrylates or polyester acrylates.
26. Alkyd resins, polyester resins and acrylate resins crosslinked with melamine resins, urea resins, isocyanates, isocyanurates, polyisocyanates or epoxy resins.
27. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.
28. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
29. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

A coating binder is for example an acid catalyzed two component system or an air drying system.

A preferred polymer for component a) is a thermoplastic polymer or a coating binder.

In particular, component a) is a thermoplastic polymer. Of high relevance is the group of thermoplastic polyolefins, especially homo- or copolymers containing polymerized propylene or ethylene. Especially preferred is polypropylene or polyethylene, very particular polyethylene.

Preferred as component a) are also biodegradable polymers of either natural or synthetic origin.

Examples are polyethylensuccinate (Lunare SE (RTM, Nihon Shokubai)), polybutylensuccinate (Bionolle 1000 (RTM, Showa Highpolymer)), polybutylensuccinate/adipate (Bionolle 3000 (RTM, Showa Highpolymer)), polybutylensuccinate/carbonate (lupec (RTM, Mitsubishi Gas Chemicals)), polybutylensuccinate/terephtalate (Biomax (RTM, Dupont), Ecoflex (RTM, BASF), EasterBio (RTM, Eastman Chemicals)), polycaprolactone (CelGreen PH (RTM, Daicel Kagaku), Tone (RTM, UCC)), poly(hydroxyalkanoates) (Nodax (RTM, Procter and Gamble), from Metabolix), poly-3-hydroxybutyrate (Biogreen (RTM, Mitsubishi Gas Chemicals)), polylactic acid (NatureWorks (RTM, Cargill), LACEA (RTM, Mitsui Chemicals), Lacty (RTM, Shimadzu Seisakusho)), polyester amides or blends of these materials with natural or modified starch, polysaccharides, lignin, wood flour, cellulose and chitin.

The employed amount of component b) in regard to component a) varies with the particular organic material and the selected application.

In general, the component b) of the present invention is employed from about 0.01 to about 10% by weight of the component a). An advantageous range is from 0.05 to 5%, in particular 0.05% to 3%. Especially preferred is 0.1% to 1.5%.

Another advantageous range is, in particular for improving flame retardancy, from 0.6% to 3%, especially from 0.7% to 1.5%.

The composition as described above comprising component a) and component b) may contain further additives.

Examples of further additives are given below:
1. Antioxidants
1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-ditert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.
1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.
1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-ditert-butyl-4-hydroxyanisole, 3,5-di-tert-butyl-4-hydroxyphenyl stearate, bis(3,5-di-tert-butyl-4-hydroxyphenyl) adipate.
1.4. Tocopherols, for example α-tocopherol, β-tocopherol, γ-tocopherol, δ-tocopherol and mixtures thereof (vitamin E).
1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)disulfide.
1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis(3,5-ditert-butyl-4-hydroxyphenyl)propane, 2,2-bis(5-tert-butyl-4-hydroxy2-methylphenyl)-4-n-dodecylmercaptobutane, 1,1,5,5-tetra-(5-tert-butyl-4-hydroxy-2-methylphenyl)pentane.
1.7. O-, N- and S-benzyl compounds, for example 3,5,3',5'-tetra-tri-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl) sulfide, isooctyl-3,5-di-tert-butyl-4-hydroxybenzylmercaptoacetate.
1.8. Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl)malonate, di-dodecylmercaptoethyl-2,2-bis(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.
1.9. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.
1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl) isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tertbutyl-4-hydroxyphenylpropionyl)-hexahydro-1,3,5-triazine, 1,3,5-tris(3,5-dicyclohexyl-4-hydroxybenzyl)isocyanurate.
1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.
1.12. Acylaminophenols, for example 4-hydroxylauranilide, 4-hydroxystearanilide, octyl N-(3,5-di-tert-butyl-4-hydroxyphenyl)carbamate.
1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.
1.14. Esters of β-(5-tert-butyl-4-hydroxy-3-methylphenyl)propionic acid with mono- or polyhydric alcohols, for example with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]undecane.
1.15. Esters of β-(3,5-dicyclohexyl-4-hydroxyphenyl) propionic acid with mono- or polyhydric alcohols, for example with methanol, ethanol, octanol, octadecanol, 1,6-hexanediol, 1,9-nonanediol, ethylene glycol, 1,2- propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, for example with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid, for example N,N'-bis(3,5-di-tert-butyl-4-hydroxyphenylpropionyl)hexamethylenediamide, N,N'-bis(3,5-di-tertbutyl-4-hydroxyphenylpropionyl) trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl] oxamide (Naugard XL-1, (RTM, supplied by Uniroyal).

1.18. Ascorbic acid (vitamin C)

1.19. Aminic antioxidants, for example N,N'-di-isopropyl-p-phenylenediamine, N,N'-di-secbutyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N-phenyl-p-phenylenediamine, 4-(p-toluenesulfamoyl) diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-ditert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl) amino]ethane, 1,2-bis(phenylamino)propane, (o-tolyl) biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octyl-phenothiazines, N-allylphenothiazine, N,N,N',N'-tetraphenyl-1,4-diaminobut-2-ene.

2. UV Absorbers and Light Stabilizers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl) benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl) benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl) phenyl)benzotriazole, 2-(3'-tert-butyl-5'-[2-(2-ethylhexyloxy)carbonylethyl]-2'-hydroxyphenyl) benzotriazole, 2-(3'-dodecyl-2'-hydroxy-5'-methylphenyl)benzotriazole, 2-(3'-tert-butyl-2'-hydroxy-5'-(2-iso-octyloxycarbonylethyl) phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300;

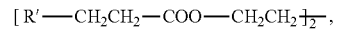

where R'=3'-tert-butyl-4'-hydroxy-5'-2H-benzotriazol-2-ylphenyl, 2-[2'-hydroxy-3'-(α,αdimethylbenzyl)-5'-(1,1,3,3-tetramethylbutyl)-phenyl]benzotriazole; 2-[2'-hydroxy-3'-(1,1,3,3-tetramethylbutyl)-5'-(α,α-dimethylbenzyl)-phenyl]benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4, 4'-dimethoxy derivatives.

2.3. Esters of substituted and unsubstituted benzoic acids, for example 4-tert-butyl-phenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxy-cinnamate, methyl α-carbomethoxy-p-methoxycinnamate, N-(β-carbomethoxy-β-cyanovinyl)-2-methylindoline, neopentyl tetra(α-cyano-β,β-diphenylacrylate.

2.5. Nickel compounds, for example nickel complexes of 2,2'-thio-bis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tertbutylbenzylphosphonic acid, nickel complexes of ketoximes, e.g. of 2-hydroxy-4-methylphenylundecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyppyrrolidine-2,5-dione, a mixture of 4-hexadecyloxy- and 4-stearyloxy-2,2,6,6-tetramethylpiperidine, a condensate of N,N-bis(2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [192268-64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl)ethene, N,N'-bis-formyl-N,N-bis(2,2,6,6-tetramethyl-4-piperidyl)hexamethylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine, 2,4-bis [N-(1-cyclohexyloxy-2,2,6,6-tetramethylpiperidine-4-yl)-N-butylamino]-6-(2-hydroxyethyl)amino-1,3,5-triazine, 1-(2-hydroxy-2-methylpropoxy)-4-octadecanoyloxy-2,2,6,6-tetramethylpiperidine, 5-(2-ethylhexanoyl)oxymethyl-3,3,5-trimethyl-2-morpholinone, Sanduvor (RTM, Clariant; CAS Reg. No. 106917-31-1], Adk Stab La-81 (CAS Reg. No. 705257-84-7), Hostavin® NOW (available from Clariant AG), Flamestab® NOR 116 (CAS Reg. No. 191680-81-6), Tinuvin® NOR 371 (mixture of oligomeric compounds which are the formal condensation products of N,N'-bis-(2,2,6,6-tetramethyl-1-propoxy-piperidin-4-yl)-hexane-1,6-diamine and 2,4-dichloro-6-{n-butyl-(2,2,6,6-tetramethyl-1-propoxy-piperidin-4-yl)-amino}-[1,3,5]triazine, end-capped with 2-chloro-4,6-bis-(di-n-butylamino)-[1,3,5]triazine), 5-(2-ethylhexanoyl)oxymethyl-3,3,5-trimethyl-2-morpholinone, the reaction product of 2,4-bis[(1-cyclohexyloxy-2,2,6,6-piperidine-4-yl)butylamino]-6-chloro-s-triazine with N,N'-bis(3-aminopropyl) ethylenediamine), 1,3,5-tris(N-cyclohexyl-N-(2,2,6,6-tetramethylpiperazine-3-one-4-yl)amino)-s-triazine, 1,3,5-tris(N-cyclohexyl-N-(1,2,2,6,6-pentamethylpiperazine-3-one yl)amino)-s-triazine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{hydroxy-4-[3-(2-ethylhexyl-1-oxy)-2-hydroxypropyloxy]phenyl}-4,6-bis(2,4-dimethylphenyl)-1,3,5-triazine, 2,4-bis(4-[2-ethylhexyloxy]-2-hydroxyphenyl)-6-(4-methoxyphenyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyldihydrazide, N,N'-bis(salicyloyl) thiopropionyl dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearylpentaerythritol diphosphite, tris(2,4-di-tert-butylphenyl) phosphite, diisodecyl pentaerythritol diphosphite, bis(2,4-di-tert-butylphenyl)pentaerythritol diphosphite, bis(2,4-di-cumylphenyl)pentaerythritol diphosphite, bis(2,6-di-tert-butyl-4-methylphenyl)pentaerythritol diphosphite, diisodecyloxypentaerythritol diphosphite, bis(2,4-di-tert-butyl methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d, g]-1,3,2-dioxaphosphocin, bis(2,4-di-tert-butyl-6-methylphenyl)methyl phosphite, bis(2,4-di-tert-butyl methylphenyl)ethyl phosphite, 6-fluoro-2,4,8,10-tetra-tert-butyl-12-methyl-dibenz[d,g]-1,3,2-dioxaphosphocin, 2,2',2''-nitrilo[triethyltris(3,3',5,5'-tetra-tert-butyl-1,1'-biphenyl-2,2'-diyl)phosphite], 2-ethylhexyl(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

The following phosphites are especially preferred:

Tris(2,4-di-tert-butylphenyl) phosphite (Irgafos 168 (RTM, Ciba Inc.), tris(nonylphenyl) phosphite,

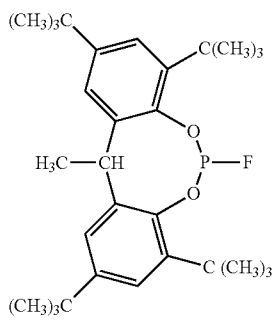
(A)

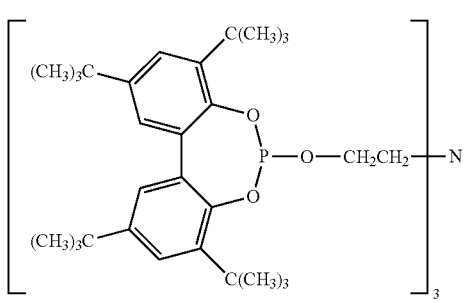
(B)

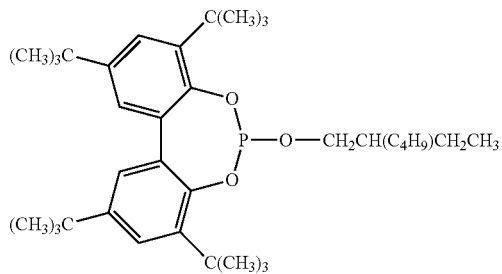
(C)

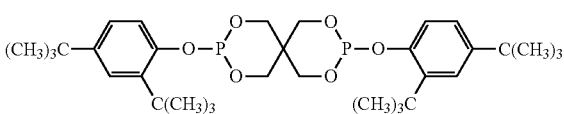
(D)

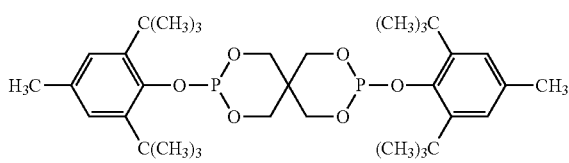
(E)

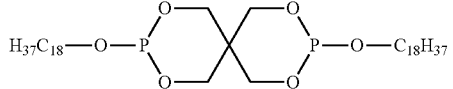
(F)

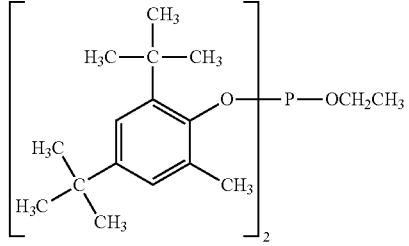
(G)

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-α-phenylnitrone, N-ethyl-α-methylnitrone, N-octyl-aheptylnitrone, N-lauryl-α-undecylnitrone, N-tetradecyl-α-tridecylnitrone, N-hexadecyl-apentadecylnitrone, N-octadecyl-α-heptadecylnitrone, N-hexadecyl-α-heptadecylnitrone, Noctadecyl-α-pentadecylnitrone, N-heptadecyl-α-heptadecylnitrone, N-octadecyl-α-hexadecylnitrone, nitrone derived from N,N-dialkylhydroxylamine derived from hydrogenated tallow amine.

7. Thiosynergists, for example dilauryl thiodipropionate, dimistryl thiodipropionate, distearyl thiodipropionate or distearyl disulfide.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis-(β-dodecylmercapto)propionate.
9. Polyamide stabilizers, for example copper salts in combination with iodides and/or phosphorus compounds and salts of divalent manganese.
10. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.
11. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers), or Irgaclear XT 386 (RTM, Ciba). Especially preferred are 1,3:2,4-bis(3',4'-dimethylbenzylidene)sorbitol, 1,3:2,4-di(paramethyldibenzylidene) sorbitol, and 1,3:2,4-di(benzylidene)sorbitol.
12. Fillers and reinforcing agents, for example calcium carbonate, silicates, glass fibres, glass beads, asbestos, talc, kaolin, mica, barium sulfate, metal oxides and hydroxides, carbon black, graphite, wood flour and flours or fibers of other natural products, synthetic fibers.
13. Other additives, for example pigments, such as carbon black, titanium dioxide in its rutile or anatase forms, color pigments; plasticisers; lubricants; emulsifiers; rheology additives; antislip/antiblock additives; catalysts; flow-control agents; optical brighteners; antistatic agents and blowing agents.
14. Benzofuranones and indolinones, for example those disclosed in U.S. Pat. Nos. 4,325,863; 4,338,244; 5,175,312; 5,216,052; 5,252,643; DE-A-4316611; DE-A-4316622; DE-A-4316876; EP-A-0589839, EP-A-0591102; EP-A-1291384 or 3-[4-(2-acetoxyethoxy) phenyl]-5,7-di-tert-butylbenzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy] phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3,4-dimethylphenyl)-5,7-di-tert-butylbenzofuran-2-one, 3-(2,3-dimethylphenyl)-5,7-di-tert-butylbenzofuran-2-one, 3-(2-acetyl-5-isooctylphenyl)-5-isooctylbenzofuran-2-one.
15. Terpene derivatives, for example those disclosed in WO 2003/080011, those mentioned in the comprehensive list of Kirk-Othmer, Encyclopedia of Chemical Technology, John Wiley & Sons, $4^{th}$ edition (1994), Vol. 23, p. 833-882.
16. Flame retardants
16.1 phosphorus containing flame retardants, for example tetraphenyl resorcinol diphosphite (Fyrolflex RDP, RTM, Akzo Nobel), tetrakis(hydroxymethyl)phosphonium sulphide, triphenyl phosphate, diethyl-N,N-bis(2-hydroxyethyl)-aminomethyl phosphonate, hydroxyalkyl esters of phosphorus acids, ammonium polyphosphate (APP), resorcinol diphosphate oligomer (RDP), phosphazene flame retardants or ethylenediamine diphosphate (EDAP).
16.2 nitrogen containing flame retardants, for example melamine-based flame retardants, isocyanurates, polyisocyanurate, esters of isocyanuric acid, like tris-(2-hydroxyethyl)isocyanurate, tris(hydroxymethyl)isocyanurate, tris(3-hydroxy-n-propyl)isocyanurate, triglycidyl isocyanurate, melamine cyanurate, melamine borate, melamine phosphate, melamine pyrophosphate, melamine polyphosphate, melamine ammonium polyphosphate, melamine ammonium pyrophosphate, dimelamine phosphate, dimelamine pyrophosphate, benzoguanamine, allantoin, glycoluril, urea cyanurate, a condensation product of melamine from the series melem, melam, melon and/or a higher condensed compound or a reaction product of melamine with phosphoric acid or a mixture thereof.
16.3 organohalogen flame retardants, for example polybrominated diphenyl oxide (DE-60F, Great Lakes), decabromodiphenyl oxide (DBDPO; Saytex 102E (RTM, Albemarle)), tris[3-bromo-2,2-bis(bromomethyl)propyl] phosphate (PB 370, (RTM, FMC Corp.)), tris(2,3-dibromopropyl)phosphate, tris(2,3-dichloropropyl)phosphate, chlorendic acid, tetrachlorophthalic acid, tetrabromophthalic acid, poly-β-chloroethyl triphosphonate mixture, tetrabromobisphenol A-bis(2,3-dibromopropyl ether) (PE68), brominated epoxy resin, ethylene-bis(tetrabromophthalimide) (Saytex BT-93 (RTM, Albemarle)), bis(hexachlorocyclopentadieno) cyclooctane (Declorane Plus (RTM, Oxychem)), chlorinated paraffins, octabromodiphenyl ether, hexachlorocyclopentadiene derivatives, 1,2-bis(tribromophenoxy)ethane (FF680), tetrabromobisphenol A (Saytex RB100 (RTM, Albemarle)), ethylene bis-(dibromonorbornanedicarboximide) (Saytex BN-451 (RTM, Albemarle)), bis-(hexachlorocycloentadeno)cyclooctane, PTFE, tris (2,3-dibromopropyl) isocyanurate or ethylene-bis-tetrabromophthalimide.

The halogenated flame retardants mentioned above are routinely combined with an inorganic oxide synergist.

16.4 inorganic flame retardants, for example aluminium trihydroxide (ATH), boehmite (A100H), magnesium dihydroxide (MDH), zinc borates, $CaCO_3$, organically modified layered silicates, organically modified layered double hydroxides, and mixtures thereof. In regard to the synergistic combination with halogenated flame retardants, the most common inorganic oxide synergists are zinc oxides, antimony oxides like $Sb_2O_3$ or $Sb_2O_5$ or boron compounds.

Preferred is a further additive selected from the group of antioxidants, UV absorbers, hindered amine light stabilizers, nickel compounds, metal deactivators, phosphites and phosphonites, hydroxylamines, thiosynergists, nucleating agents, peroxide scavengers, fillers or reinforcing agents and terpene derivatives.

Especially preferred is a composition which comprises components a), b), a metal oxide and a phenolic antioxidant selected from the lists 1.1-1.18 as provided above. An especially preferred metal oxide in such a combination is zinc oxide.

Particularly preferred is a composition which comprises components a), b) and a phenolic antioxidant selected from the lists 1.1-1.18 as provided above.

Very preferred phenolic antioxidants in these compositions are esters of β-(3,5-di-tertbutyl-4-hydroxyphenyl)propionic acid with mono- or polyhydric alcohols (i.e. list 1.13.). Especially preferred are tetrakis-[3-(3,5-di-tert-butyl- 4-hydroxy-phenyl)-propionyloxymethyl]-methane and 3-(3,5-di-tert-butyl-4-hydroxy-phenyl)-propionic acid octadecyl ester.

Preferred is a composition which comprises components a), b), a phenolic antioxidant selected from the lists 1.1-1.18 as provided above, a phosphite stabilizer selected from the list 4 as provided above and a basic costabilizer selected from the list 10 as provided above. Especially preferred is the composition, wherein said basic costabilizer is calcium stearate.

Preferred is further a composition comprising a flame retardant selected from the group consisting of phosphorus containing flame retardants, nitrogen containing flame retardants, organo halogen flame-retardants and inorganic flame retardants, for example as those given in the above lists 16.1 to 16.4.

More preferred are the following flame retardants: tris(tribromoneopentyl)phosphate, resorcinol-bis-diphenylphosphate, pentaerythritol-di-methyl phosphonate, guanidine phenylphosphonate, melamine phenylphosphonate, dimethylaluminium phosphinate, methyl-ethylaluminiumphosphinate, diethylaluminiumphosphinate, poly-[2,4-(piperazine-1,4-yl)-6-morpholine-4-yl)-1,3,5-triazine] and ammonium polyphosphate.

The optional further additive in the stabilized compositions of the invention may be contained from 0.01% to 5%, preferably from 0.025% to 2%, and especially from 0.1% to 1% by weight of the stabilized composition.

In case of a flame retardant as optional further additive, the flame retardant is advantageously contained in the composition of the invention in an amount from 0.5% to 60.0% by weight of the organic material; for instance from 1.0% to 40.0%; for example from 5.0% to 35.0% by weight of the organic material.

The component b) as well as an optional further additive of the invention may readily be incorporated into the organic material as component a) by conventional techniques, at any convenient stage prior to the manufacture of shaped articles therefrom.

The component b) as well as an optional further additive can judiciously be incorporated by one of the following methods:
as emulsion or dispersion (e.g. to latices or emulsion polymers)
as a dry mixture during the blending
by direct introduction into the processing apparatus (e.g. extruders, internal mixers)
as solution in an organic solvent
as melt.

The organic material as component a) can be in the form of a solid, solution, suspension or emulsion.

Incorporation of the component b) as well as an optional further additive is in case of thermoplastic polymers as component a) performed best in a thermal compounding step. Thorough blending of the component a), component b) as well as an optional further additive is followed by an extrusion of the physical blend at elevated temperature. Typically an extruder with suitable screw configuration is used for this step.

The additives can also be added to the polymer as component a) in the form of a masterbatch ('concentrate'), which contains the component b) as well as an optional further additive incorporated in a further polymer of the masterbatch. The concentration for the additives is, for example, from 1% to 50%, in particular 2.5% to 30% by weight of the masterbatch. Said further masterbatch polymer must not be necessarily of identical structure than the polymer as component a). The masterbatch polymer can be produced in a different manner to that of the polymer as component a). The masterbatch can be in the form of a powder, granules, solutions, suspensions or in the form of latices.

In case of a polymer as component a), the polymer compositions of this invention can be employed in various forms and/or processed to give various final products, for example as to obtain films, fibres, tapes, moulding compositions, profiles or as binders for coating materials, adhesives or putties.

In more detail, the final product respectively article can be any type of polymeric article, which needs stabilization in natural sunlight and/or humidity at low, ambient or elevated temperature. For example, the polymer component may be used to manufacture polymeric films, sheets, bags, bottles, pipes, cables, styrofoam cups, plates, utensils, blister packages, boxes, package wrappings, plastic fibers, tapes, agricultural articles such as twines, cover films, mulch films, small tunnel films, films or silage, silobags, stretched bale wraps, banana bags, direct covers, nonwoven, pots for agricultural use, geotextiles, landfill covers, industrial covers, waste covers, temporary scaffolding sheets, building films, silt fences, poultry curtains, films for building temporary shelter constructions, disposable diapers, disposable garments or the like.

The polymeric articles may be manufactured by any process available to those of ordinary skill in the art including, but not limited to, extrusion, extrusion blowing, film casting, film blowing, calendering, injection molding, blow molding, compression molding, thermoforming, spinning, blow extrusion or rotational casting.

For the production of the desired polymeric article out of the polymer compositions of this invention, any appropriate equipment can be used, depending on the final form of the article, for example a blow extruder in the case of films, an extrusion machine in the case of sheets or an injection molding machine.

The mixtures of the compounds of formulae (1) and (2), as well as the compounds of formula (2), are excellent stabilizers against the harmful effect of light and heat and oxidation in different applications like, but not limited, to agriculture, with or without the use of pesticides. The mixtures are also excellent flame retardants.

A further embodiment of this invention is a method for stabilization of an organic material susceptible to oxidative, thermal or light-induced degradation, which comprises the incorporation therein or applying thereto the additive mixture of formulae (1) and (2).

Preferred is also the use of the additive mixture of formulae (1) and (2) for stabilization of an organic material susceptible to oxidative, thermal or light-induced degradation.

As to the compounds of formulae (1) and (2) the definitions and preferences given hereinbefore apply.

A further embodiment of this invention is a method for improving flame retardancy of an organic material, which comprises the incorporation therein or applying thereto the additive mixture of formulae (1) and (2). Preferred is also the use of the additive mixture of formulae (1) and (2) for improving the flame retardancy of an organic material.

As to the compounds of formulae (1) and (2) the definitions and preferences given hereinbefore apply.

A further embodiment of this invention is a method for stabilization of an organic material susceptible to oxidative, thermal or light-induced degradation, which comprises the incorporation therein or applying thereto a compound of formula (2).

Preferred is also the use of the compound of formula (2) for stabilization of an organic material susceptible to oxidative, thermal or light-induced degradation.

As to the compound of formula (2) the definitions and preferences given hereinbefore apply.

Another aspect of this invention is a process for the preparation of a compound of formula 1')

to an oxidation reaction, followed by a hydrogenation reaction, wherein $R_1$, $R_2$, $R_3$, $R_4$, $R'_1$, $R'_2$, $R'_3$ and $R'_4$ are independently from each other hydrogen or $C_1$-$C_{18}$ alkyl, $X_1$ and $X'_1$ are independently from each other $C_2$-$C_{12}$ alkylene or $C_3$-$C_{12}$ alkylene substituted by hydroxyl;

one to five radicals of the radicals $Z_1$, $Z_2$, $Z_3$, $Z_4$, $Z_5$ and $Z_6$ are a group of formula —O—$CH_2$—$CH_2$—$CH_2$—R and the remaining of the radicals $Z_1$, $Z_2$, $Z_3$, $Z_4$, $Z_5$ and $Z_6$ are hydrogen or hydroxy, especially hydrogen,

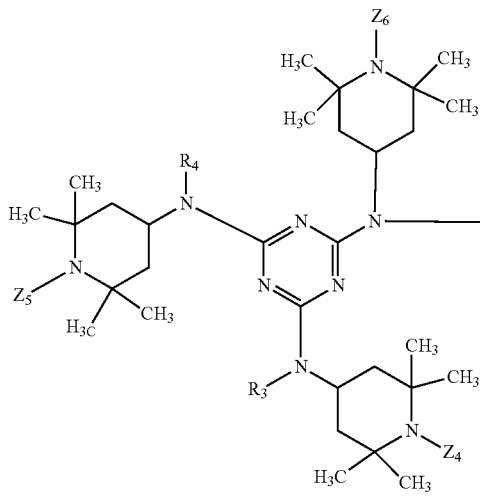
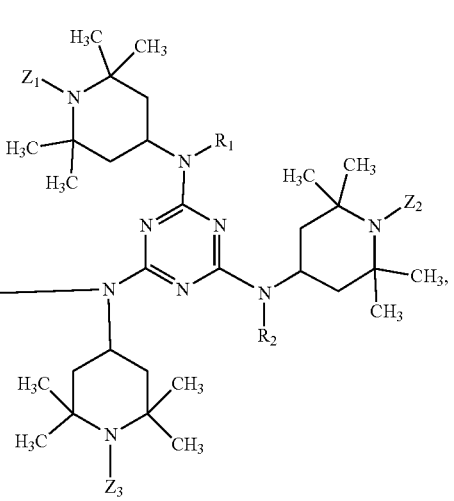

(1')

comprising subjecting a compound of formula (2)

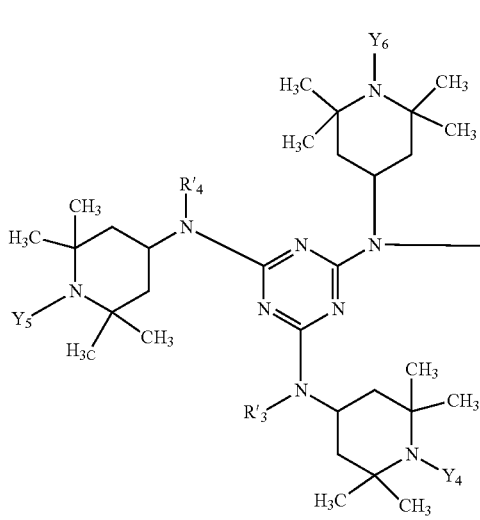
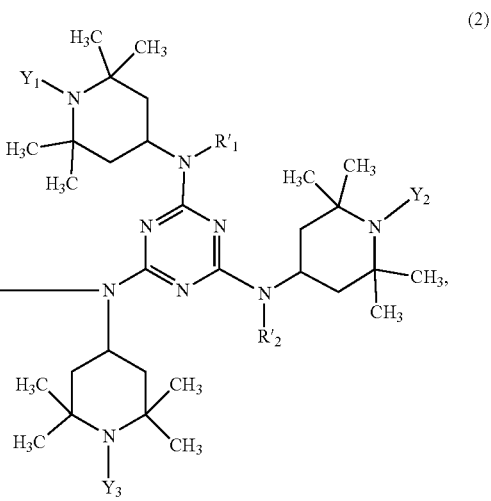

(2)

one to five radicals of the radicals $Y_1, Y_2, Y_3, Y_4, Y_5$ and $Y_6$ are a group of formula —$CH_2$—CH=CH—R and the remaining of the radicals $Y_1, Y_2, Y_3, Y_4, Y_5$ and $Y_6$ are hydrogen, and R is hydrogen or $C_1$-$C_{15}$ alkyl. R is preferably hydrogen.

Preferences given hereinbefore shall apply to the compounds of formulae (1') and (2) of the above preparation process, as applicable. Highly preferred for these compounds are those of formulae (1-A) and (2-A), wherein the substituents are defined as given for the above preparation process, and for which substituents in addition applicable preferences given hereinbefore shall apply.

Compounds of formula (2), which are used for the preparation of compounds of formula (1') can, for example, be prepared by reacting a corresponding compound of formula (3)

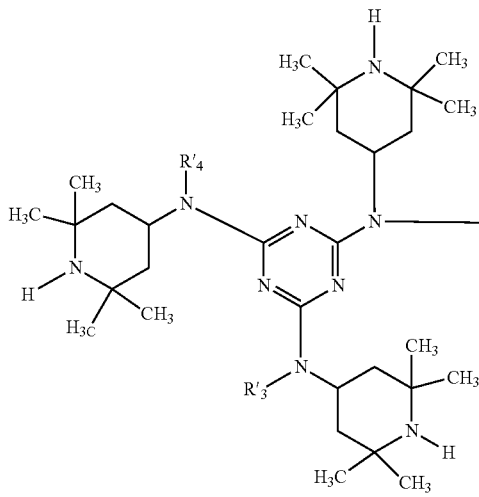
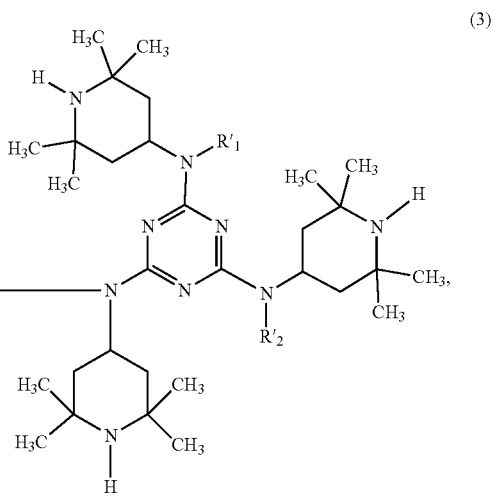

(3)

wherein $R'_1$, $R'_2$, $R'_3$, $R'_4$ and $X'_1$ are defined as given above for formula (2), with an allyl halide of formula

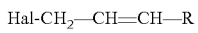

(4), wherein Hal is halogen, preferably chlorine or especially bromine, and R is as defined above.

The reaction may, for example, be carried out in presence of an organic solvent, like xylene, toluene, mesitylene or ethylbenzene, especially xylene or toluene. A base is usually added, like sodium carbonate, potassium carbonate, sodium hydroxide or sodium phosphate, preferably sodium carbonate or potassium carbonate. It is preferred to carry out the reaction at a temperature of 130° C. to 180° C., especially 130° C. to 160° C. Instead of an allyl halide of formula (4) also corresponding allyl alcohols or ally carbonates could be used.

The allyl halide is, as a rule, used in sub-stochiometric amounts, since for the preparation of the compounds of formula (1') there are used compounds of formula (2), wherein only one to five of the radicals $Y_1, Y_2, Y_3, Y_4, Y_5$ and $Y_6$ are a group of formula —$CH_2$—CH=CH—R. For example, for the preparation of compounds of formula (2), wherein five of the radicals $Y_1, Y_2, Y_3, Y_4, Y_5$ and $Y_6$ are a group of formula —$CH_2$—CH=CH—R, an amount of about ⅚ of the stochiometric amount of the allyl halide may be used.

The allyl halide may preferably be used in amounts, which are 40 to 95%, especially 40 to 90% of the stochiometric amount. More preferred is an amount of 50 to 90%, especially 60 to 90% of the stochiometric amount.

The compound of formula (3) can be prepared according to known methods or in analogy to known methods, for example as described in WO 2011/029744, Example 1.

If desired, the compounds of formula (2) may be isolated, for example by removing the organic solvent under reduced pressure.

For a further reaction it is preferred to use the reaction mixture without isolation, as obtained after the above reaction of compound of formula (3) with the allyl halide of formula (4).

For the preparation of the compound of formula (1') the compound of formula (2) is subjected to an oxidation reaction, followed by a hydrogenation reaction.

Oxidation is usually carried out with peracetic acid. Alternatively also hydrogen peroxide, meta-chloroperoxybenzoic acid or tert-butyl hydroperoxide may be used. The reaction may, for example, be carried out in presence of an organic solvent, like xylene, toluene, mesitylene or ethylbenzene, especially xylene or toluene. Also, dichloromethane may be used. A base, like sodium carbonate, sodium hydrogen carbonate, potassium carbonate, sodium hydroxide or sodium phosphate, especially sodium carbonate or potassium carbonate, is usually used. It is preferred to carry out the reaction at a temperature of 0° C. to 40° C., especially 0° C. to 30° C. According to the oxidation step groups of formula —$CH_2$—CH=CH—R should be converted to groups of formula —O—$CH_2$—CH=CH—R.

If desired, the resulting intermediates may be isolated, for example by removing the organic solvent under reduced pressure. For a further reaction it is preferred to use the reaction mixture without isolation, as obtained after the above oxidation step.

Hydrogenation is usually carried out with hydrogen. As catalyst it is preferred to use palladium. Alternative catalysts could be Pt, Rh, Ru or Ni. The catalyst loading could be 0.05 to 2 weight-%. The reaction may, for example, be carried out in presence of an organic solvent, like xylene, toluene, mesitylene, ethylbenzene, methanol, especially toluene or xylene. It is also possible to use water. It is preferred to carry out the reaction at a temperature of 50° C. to 90° C., especially 60° C. to 80° C. The hydrogen pressure could be 10 to 50 bar.

The resulting compounds of formula (1') may be isolated, for example by removing the organic solvent under reduced pressure.

EXAMPLES

Synthesis and Preparation Examples

Example 1: Synthesis of compound of formula (1-A), wherein 70 mole-% of $Z_1$, $Z_2$, $Z_3$, $Z_4$, $Z_5$ and $Z_6$ are n-propyloxy and the remaining of these radicals are hydrogen or hydroxy. In the following this compound is referred to as compound (101).
a) Synthesis of compound of formula (2-A), wherein 80 mole-% of $Y_1$, $Y_2$, $Y_3$, $Y_4$, $Y_5$ and $Y_6$ are an allyl group and the remaining of these radicals are hydrogen. In the following this compound is referred to as compound (201).

In a one liter autoclave equipped with a mechanical stirrer 0.94 mol of $Na_2CO_3$ and 0.14 mol of the compound of formula (301)

of water are added and the mixture is warmed up and stirred at 75° C. for 1 hour. The organic phase is separated, washed with 0.07 mol of $Na_2CO_3$ and 5.56 mol of water. The organic phase is directly used in the following step without any further purification. Conversion: 93%
c) Final synthesis of compound (101)
From the reaction mixture as obtained according to the above step b) solvent is removed to get a final concentration between 45 and 60 weight-%. The solution is loaded in a one liter autoclave together with 0.14 mmol of Pd/C (5 weight-%) The overall mixture is heated at 70° C. under 30 bar hydrogen for 4 hours.

The solution is cooled to room temperature, filtered to remove the catalyst and dried under reduced pressure. A slightly pinkish solid is obtained. Conversion: 98%. Softening range: 110-150° C.

Example 2: Synthesis of compound of formula (2-A), wherein all of $Y_1$, $Y_2$, $Y_3$, $Y_4$, $Y_5$ and $Y_6$ are an allyl group. In the following this compound is referred to as compound (202).

Synthesis is carried out according to Example 1 a), but using 1.29 mol of allyl bromide (instead of 0.79 mol of allyl bromide).

Compound (202) is isolated removing the solvent under reduced pressure to get a solid.

Example 3: Synthesis of compound of formula (2-A), wherein 50 mole-% of $Y_1$, $Y_2$, $Y_3$, $Y_4$, $Y_5$ and $Y_6$ are an

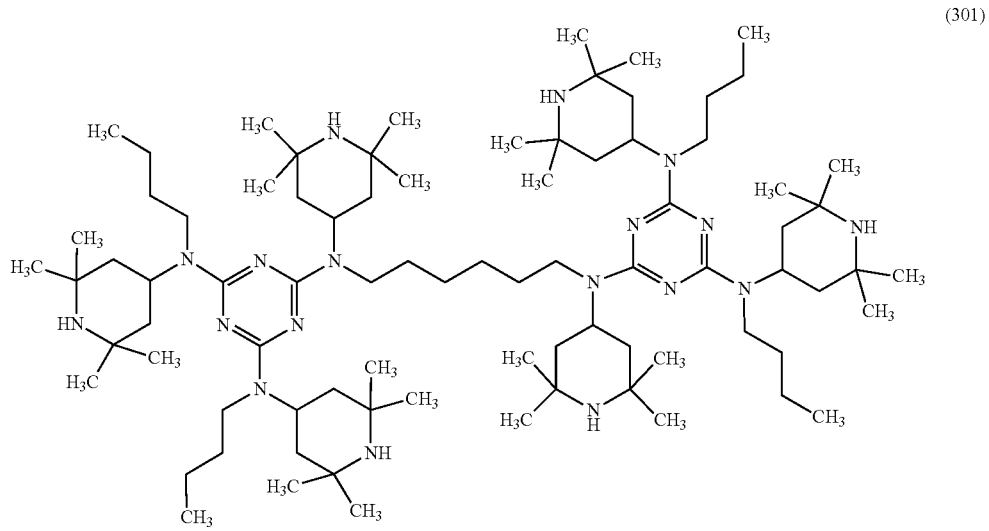

(301)

allyl group and the remaining of these radicals are hydrogen. In the following this compound is referred to as compound (203).

Synthesis is carried out according to Example 1 a), but adjusting the amount of allyl bromide used accordingly.

Example 4: Preparation of mixtures

Compounds (101), (201), (202) and (203) are isolated as given in Example 2 above. The mixtures given in the following Application Example 1, Table 1, are prepared by homogenously mixing the solids of the corresponding compounds in the indicated weight ratio.

Alternatively, it is also possible to mix directly the reaction mixtures of the compounds to be mixed, and then to remove the solvent under reduced pressure to get solid mixtures.

dissolved in xylene to reach 45 weight-% concentration are added, then 0.79 mol of allyl bromide are added. The mixture is heated at 145° C. for 7 hours, cooled down to 60° C. and washed with 26.7 mol of water at 85° C. A second washing is performed with 0.05 mol of $Na_2CO_3$ dissolved in 11.1 mol of water. The organic phase is directly used in the following step without any further purification. Conversion: 80%.
b) Oxidation of compound of formula (201)
The reaction mixture as obtained according to the above step a) is diluted to 32 weight-% concentration with xylene and is placed in a glass reactor equipped with a mechanical stirrer, thermocouple and a dropping funnel. 1.13 mol of $Na_2CO_3$ are added. The suspension is cooled down to 0° C. and 0.86 mol of peracetic acid solution (35 weight-% in water) is slowly added over 3 hours. Afterwards, 16.7 mol

APPLICATION EXAMPLES

Application Example 1: Stabilization of LDPE (Low Density Polyethylene) Multi-Layer Films Masterbatch formulations are prepared, containing 10% by weight in total of the light stabilizer(s) indicated in Table 1 below, 0.4% by weight of tris{2,4-di-tert-butylphenyl} phosphite and 0.1% by weight of octadecyl 3-(3,5-di-tert-butyl-4-hydroxyphenyl)propionate as process stabilizers, and the rest of polyethylene powder (Polimeri Europa Riblene® FC 30, characterized by a density of 0.922 g/cm$^3$ and a melt flow index (190° C./2.16 Kg) of 0.27 g/10 min). The masterbatch formulations are mixed in a turbo-mixer. Each masterbatch formulation is extruded at a maximum temperature of 200° C. in a lab-scale OMC twin-screw extruder (Ø 19 mm, L/D=25). 360 g of the granules so obtained for each masterbatch formulation are mixed with 30 g of a polyethylene masterbatch containing 0.4% by weight of tris{2,4-di-tert-butylphenyl} phosphite and 0.1% by weight of octadecyl 3-(3,5-di-tert-butyl-4-hydroxyphenyl)propionate as process stabilizers and with 5610 g of the above indicated virgin polyethylene in pellets, in a Rhon-rad® slow mixer for 10 minutes, resulting in the final formulation that contains 0.6% in total of the light stabilizer(s) indicated in Table 1 below. Then, each final formulation is blown in a lab-scale Collin® 5-layer blow-extruder (Ø 20-25-30 mm, L/D 25), at a maximum temperature of 210° C., to give a 5-layer film of overall 150 µm thickness (45-5-50-5-45 µm), having the same formulation in all layers. The following formulations are prepared:

TABLE 1

| Formulation | | Light stabilizer(s) |
|---|---|---|
| 1C | Comparative Formulation | 0.6% by weight of compound (301) |
| 2 | Inventive Formulation | 0.6% by weight of compound (201) |
| 3C | Comparative Formulation | 0.3% by weight of compound (301) 0.3% by weight of compound (101) |
| 4 | Inventive Formulation | 0.3% by weight of compound (203) 0.3% by weight of compound (101) |
| 5 | Inventive Formulation | 0.3% by weight of compound (201) 0.3% by weight of compound (101) |
| 6 | Inventive Formulation | 0.3% by weight of compound (202) 0.3% by weight of compound (101) |

Application Example 2

Film specimens for each formulation are exposed in a Q-Panel QUV/se piece of equipment (QUV, as per ASTM G154, 1.55 W/m2 at 340 nm, cycle 6) for accelerated light weathering. Such specimens are taken at defined intervals and evaluated for embrittlement. The longer the time to embrittlement the better the stabilizing effect from the sterically hindered stabilizers in the different formulations. The results are reported in Table 2 below. It can be observed that formulation 2, based on compound (201) object of the present invention, is better than formulation 1C and that formulations 4, 5 and 6, based on mixtures with compound (201) or its homologues, are better than formulation 3C.

TABLE 2

| Formulation | Time to embrittlement (hours) |
|---|---|
| 1C | 4991 |
| 2 | 7034 |
| 3C | 7034 |
| 4 | 7528 |
| 5 | 8490 |
| 6 | 8490 |

Higher times to embrittlement are desired.

Application Example 3

This test is aimed at combining light irradiation and use of agrochemicals known to have a detrimental effect on the light stability performance of the light stabilizers contained in them. To achieve such a purpose, an agrochemical treatment is carried out on the prepared films before artificial weathering. Specimens of the films for each formulation are mounted on a small experimental greenhouse (geographical coordinates: Lat. 44° 25'40"N Long. 11° 16'39"E), inside of which a treatment with metam sodium, a sulfur-based fumigant used in agricultural practice, is carried out. After the treatment the small greenhouse is covered with a single piece of opaque film to block the direct exposure of the sample to sunlight, in order to minimize in turn the effects of solar irradiation and hence the possible differences on samples exposed in subsequent test series. The experimental conditions are closely monitored, so as to obtain the desired level of contamination from sulfur in the film samples, measured by Inductively Coupled Plasma.

After the agrochemical treatment, the film specimens for each formulation are exposed in an Atlas Weather-O-Meter (WOM, as per ASTM G155, 0.35 W/m2 at 340 nm, dry cycle), for accelerated light weathering. Specimens of the required formulations are taken at defined intervals of time after exposure and undergo carbonyl increment evaluation. The carbonyl increment is measured by means of a Perkin-Elmer® Spectrum 100 FT-IR spectrophotometer, as a measure of the oxidation degree of the polymer, so low levels of carbonyl are desired. The results are reported in table 3. It can be observed that formulation 2, based on compound (201) object of the present invention, is better than formulation 1C and that formulations 4, 5 and 6, based on mixtures with compound (201) or its homologues, are better than formulation 3C.

TABLE 3

| Formulation | Carbonyl increment after 2992 WOM exposure |
|---|---|
| 1C | 0.076 |
| 2 | 0.041 |
| 3C | 0.067 |
| 4 | 0.051 |
| 5 | 0.045 |
| 6 | 0.036 |

Low carbonyl increment is desired.

Application Example 4

An agrochemical treatment is carried out, as described in Application Example 3. After the agrochemical treatment, the film specimens for each formulation are exposed in an Atlas Weather-O-Meter (WOM, as per ASTM G155, 0.35

W/m2 at 340 nm, dry cycle), for accelerated light weathering. Specimens of the required formulations are taken at defined intervals of time after exposure and undergo the evaluation of the mechanical properties. The residual elongation at break is measured, by means of a Zwick® Z1.0 constant velocity tensiometer (as per modified ISO 527), in order to evaluate the decay of the mechanical properties of the plastic film, as a consequence of the polymer degradation after its oxidation.

The results are reported in Table 4.

TABLE 4

| Formulation | Time in hours to reach 50% of the initial elongation to break |
|---|---|
| 1C | 1698 |
| 2 | 2492 |
| 3C | 7058 |
| 5 | 7564 |
| 6 | 8183 |

High values are desired.

Application Example 5

Like Application Example 3, this test is aimed at combining light irradiation and use of agrochemicals. In this test too, an agrochemical treatment is carried out on the prepared films before artificial weathering. Specimens of the films for each formulation are mounted outdoor in an experimental cabinet (geographical coordinates: Lat. 44° 25'40"N Long. 11° 16'39"E), inside of which some burners of the type used in common agricultural practice are placed to allow sublimation of elemental sulfur, a widely used fungicide. The so-called "sulfur burning" is carried out so as to burn a specific weighted amount of sulfur. The amount of burnt sulfur is regulated and the weathering conditions closely monitored, so as to obtain the desired level of contamination from sulfur in the film samples, measured by Inductively Coupled Plasma.

After the agrochemical treatment, the film specimens for each formulation are exposed in an Atlas Weather-O-Meter (WOM, as per ASTM G155, 0.35 W/m2 at 340 nm, dry cycle), for accelerated light weathering. Specimens of the required formulations are taken at defined intervals of time after exposure and undergo carbonyl increment evaluation. The carbonyl increment is measured by means of a Perkin-Elmer® Spectrum 100 FT-IR spectrophotometer, as a measure of the oxidation degree of the polymer. The results are reported in Table 4 below. It can be observed that formulation 5, based on mixture between compound (201) and compound (101), object of the present invention, is better than formulation 3C, showing a better light stabilization, when in presence of agrochemical treatment.

TABLE 5

| Formulation | Carbonyl increment after 2502 WOM exposure |
|---|---|
| 3C | 0.143 |
| 5 | 0.094 |

Low carbonyl increment is desired.

Application Example 6

An agrochemical treatment is carried out, as described in Application Example 5. After the agrochemical treatment, the film specimens for each formulation are exposed in an Atlas Weather-O-Meter (WOM, as per ASTM G155, 0.35 W/m2 at 340 nm, dry cycle), for accelerated light weathering. Specimens of the required formulations are taken at defined intervals of time after exposure and undergo the evaluation of the mechanical properties, as described in Application Example 4. The results are reported in Table 6 below.

TABLE 6

| Formulation | Time in hours to reach 50% of the initial elongation to break |
|---|---|
| 3C | 2628 |
| 5 | 3098 |

High values are desired.

The invention claimed is:

1. An additive mixture comprising a compound of formula (1)

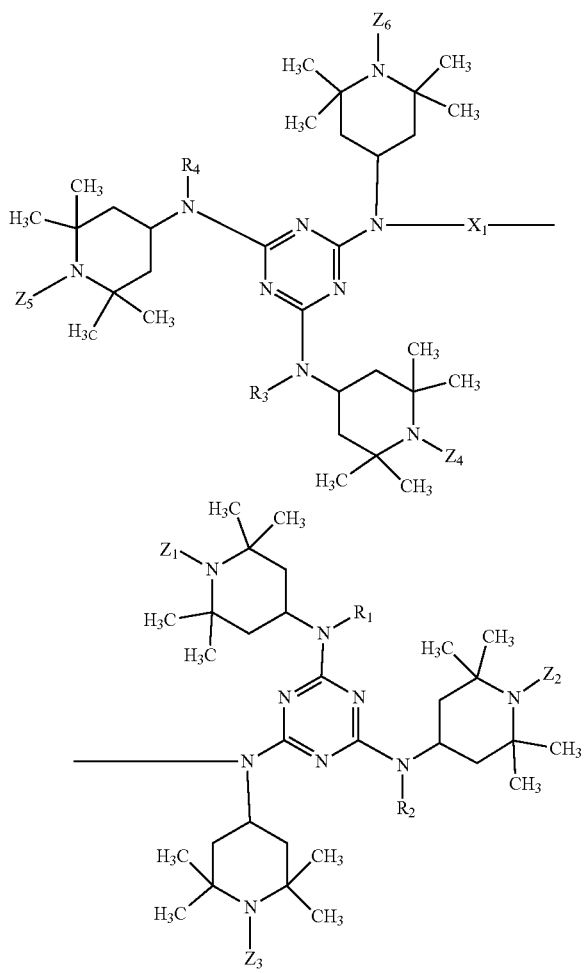

and a compound of formula (2)

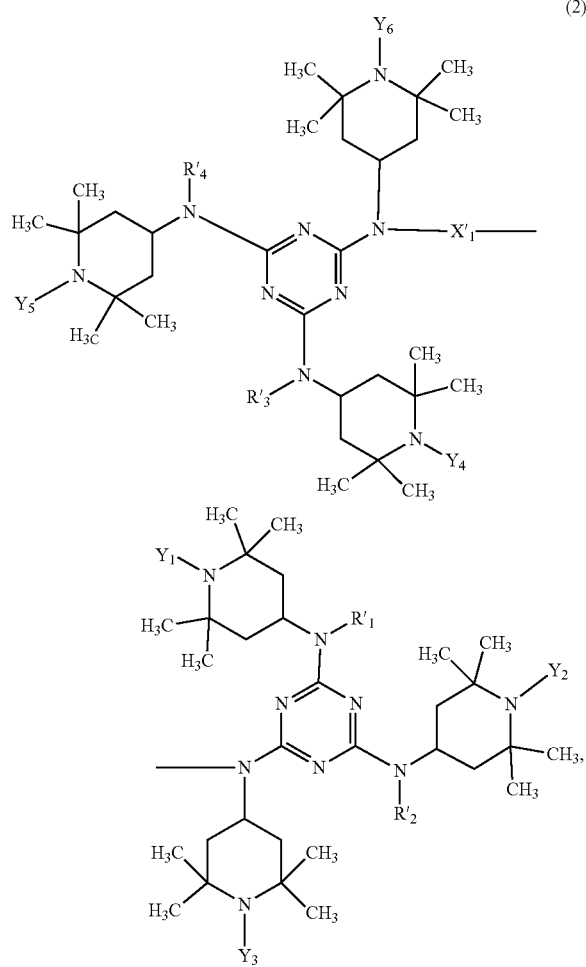

wherein
$R_1$, $R_2$, $R_3$, $R_4$, $R'_1$, $R'_2$, $R'_3$ and $R'_4$ are independently from each other hydrogen or $C_1$-$C_{18}$ alkyl,
$X_1$ and $X'_1$ are independently from each other $C_2$-$C_{12}$ alkylene or $C_3$-$C_{12}$ alkylene substituted by hydroxyl;
at least one of the radicals $Z_1$, $Z_2$, $Z_3$, $Z_4$, $Z_5$ and $Z_6$ is $C_1$-$C_{18}$ alkyloxy or $C_5$-$C_7$ cycloalkyloxy and the remaining of the radicals $Z_1$, $Z_2$, $Z_3$, $Z_4$, $Z_5$ and $Z_6$ are independently from each other hydrogen, hydroxy, $C_1$-$C_{18}$ alkyloxy or $C_5$-$C_7$ cycloalkyloxy, and
at least one of the radicals $Y_1$, $Y_2$, $Y_3$, $Y_4$, $Y_5$ and $Y_6$ is a group of formula —$CH_2$—CH=CH—R and the remaining of the radicals $Y_1$, $Y_2$, $Y_3$, $Y_4$, $Y_5$ and $Y_6$ are independently from each other hydrogen or a group of formula —$CH_2$—CH=CH—R, wherein R is hydrogen, $C_1$-$C_{18}$ alkyl or $C_5$-$C_7$ cycloalkyl.

2. An additive mixture according to claim 1, wherein $R_1$, $R_2$, $R_3$, $R_4$, $R'_1$, $R'_2$, $R'_3$ and $R'_4$ are $C_1$-$C_{12}$ alkyl.

3. An additive mixture according to claim 1, wherein $X_1$ and $X'_1$ are $C_2$-$C_8$ alkylene.

4. An additive mixture according to claim 1, wherein one to five radicals of the radicals $Z_1$, $Z_2$, $Z_3$, $Z_4$, $Z_5$ and $Z_6$ are $C_1$-$C_{18}$ alkyloxy or $C_5$-$C_7$ cycloalkyloxy and the remaining of the radicals $Z_1$, $Z_2$, $Z_3$, $Z_4$, $Z_5$ and $Z_6$ are hydrogen or hydroxy.

5. An additive mixture according to claim 1, wherein $Z_1$, $Z_2$, $Z_3$, $Z_4$, $Z_5$ and $Z_6$ in the meaning as $C_1$-$C_{18}$ alkyloxy are a group of formula —O—$CH_2$—$CH_2$—$CH_2$—R, wherein R is hydrogen or $C_1$-$C_{15}$ alkyl.

6. An additive mixture according to claim 1, wherein one to five radicals of the radicals $Y_1$, $Y_2$, $Y_3$, $Y_4$, $Y_5$ and $Y_6$ are a group of formula —$CH_2$—CH=CH—R and the remaining of the radicals $Y_1$, $Y_2$, $Y_3$, $Y_4$, $Y_5$ and $Y_6$ are hydrogen.

7. An additive mixture according to claim 1, wherein R is hydrogen.

8. An additive mixture according to claim 1, wherein
$R_1$, $R_2$, $R_3$, $R_4$, $R'_1$, $R'_2$, $R'_3$ and $R'_4$ are $C_1$-$C_{12}$ alkyl,
$X_1$ and $X'_1$ are $C_2$-$C_8$ alkylene,
one to five radicals of the radicals $Z_1$, $Z_2$, $Z_3$, $Z_4$, $Z_5$ and $Z_6$ are $C_1$-$C_{18}$ alkyloxy or $C_5$-$C_7$ cycloalkyloxy and the remaining of the radicals $Z_1$, $Z_2$, $Z_3$, $Z_4$, $Z_5$ and $Z_6$ are hydrogen or hydroxy,
one to five radicals of the radicals $Y_1$, $Y_2$, $Y_3$, $Y_4$, $Y_5$ and $Y_6$ are a group of formula —$CH_2$—CH=CH—R and the remaining of the radicals $Y_1$, $Y_2$, $Y_3$, $Y_4$, $Y_5$ and $Y_6$ are hydrogen, and
R is hydrogen.

9. An additive mixture according to claim 1, wherein the weight ratio of compound of formula (1) to compound of formula (2) is 5:95 to 95:5.

10. A composition comprising
a) an organic material which is susceptible to oxidative, thermal or light-induced degradation; and
b) an additive mixture as defined in claim 1.

11. A method for stabilization of an organic material susceptible to oxidative, thermal or light-induced degradation, comprising incorporating an additive mixture as defined in claim 1 in the organic material or applying an additive mixture as defined in claim 1 to the organic material.

12. A method for improving flame retardancy of an organic material, comprising incorporating an additive mixture as defined in claim 1 in the organic material or applying an additive mixture as defined in claim 1 to the organic material.

13. A method for stabilization of an organic material susceptible to oxidative, thermal or light-induced degradation, comprising incorporating a compound of formula (2) as defined in claim 1 in the organic material or applying a compound of formula (2) as defined in claim 1 to the organic material.

14. A process for the preparation of a compound of formula (1')

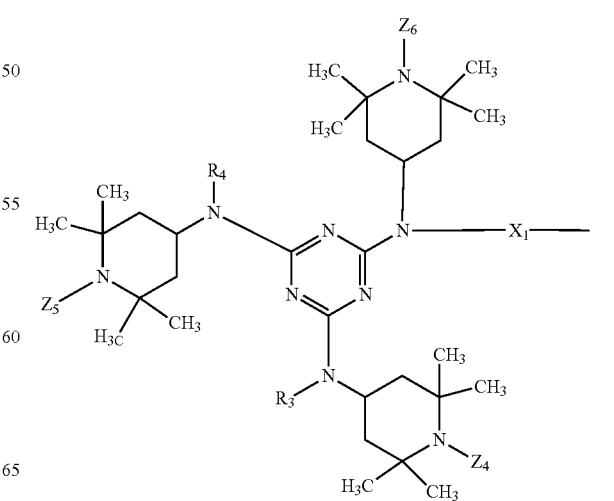

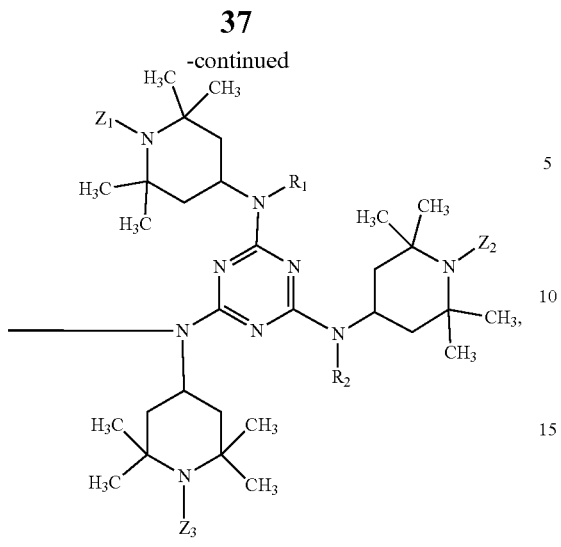
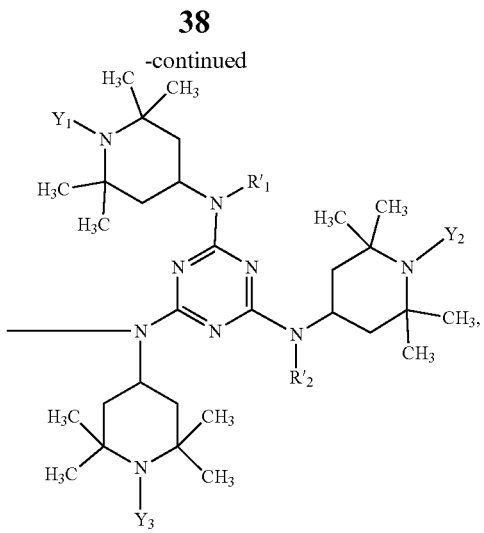

comprising subjecting a compound of formula (2)

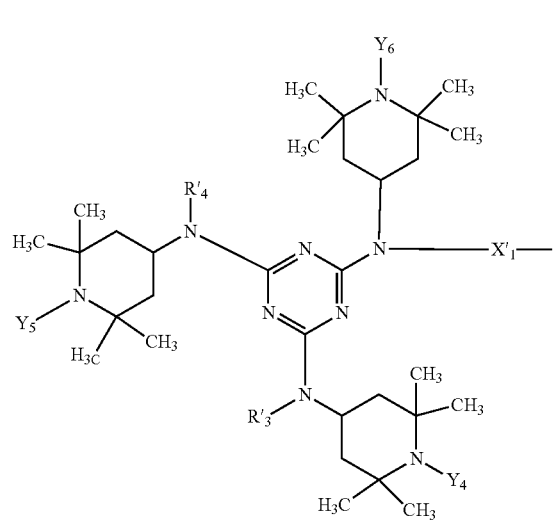

(2)

to an oxidation reaction, followed by a hydrogenation reaction, wherein $R_1$, $R_2$, $R_3$, $R_4$, $R'_1$, $R'_2$, $R'_3$ and $R'_4$ are independently from each other hydrogen or $C_1$-$C_{18}$ alkyl, $X_1$ and $X'_1$ are independently from each other $C_2$-$C_{12}$ alkylene or $C_3$-$C_{12}$ alkylene substituted by hydroxyl;

one to five radicals of the radicals $Z_1$, $Z_2$, $Z_3$, $Z_4$, $Z_5$ and $Z_6$ are a group of formula —O—$CH_2$—$CH_2$—$CH_2$—R and the remaining of the radicals $Z_1$, $Z_2$, $Z_3$, $Z_4$, $Z_5$ and $Z_6$ are hydrogen or hydroxy, one to five radicals of the radicals $Y_1$, $Y_2$, $Y_3$, $Y_4$, $Y_5$ and $Y_6$ are a group of formula —$CH_2$—CH=CH—R and the remaining of the radicals $Y_1$, $Y_2$, $Y_3$, $Y_4$, $Y_5$ and $Y_6$ are hydrogen, and R is hydrogen or $C_1$-$C_{15}$ alkyl.

* * * * *